(12) United States Patent
Butler et al.

(10) Patent No.: US 7,696,394 B2
(45) Date of Patent: Apr. 13, 2010

(54) TREATMENT OF ALKYLATION CATALYST POISONS WITH DEHYDROGENATION

(75) Inventors: James R. Butler, League City, TX (US); Marcus Ledoux, Baton Rouge, LA (US); Michael Betbeze, Baton Rouge, LA (US)

(73) Assignee: Fina Technology, Inc., Houston, TX (US)

( * ) Notice: Subject to any disclaimer, the term of this patent is extended or adjusted under 35 U.S.C. 154(b) by 17 days.

(21) Appl. No.: 12/327,682

(22) Filed: Dec. 3, 2008

(65) Prior Publication Data

US 2009/0149685 A1     Jun. 11, 2009

Related U.S. Application Data

(63) Continuation of application No. 11/361,817, filed on Feb. 24, 2006, now abandoned.

(60) Provisional application No. 60/656,464, filed on Feb. 25, 2005.

(51) Int. Cl.
*C06C 2/58* (2006.01)
*C07C 5/327* (2006.01)

(52) U.S. Cl. .............. 585/323; 585/467; 585/440; 585/441

(58) Field of Classification Search .......... 585/323, 585/467, 440, 441
See application file for complete search history.

(56) References Cited

U.S. PATENT DOCUMENTS 7,094,939 B1 * 8/2006 Jeanneret .................. 585/323

* cited by examiner

*Primary Examiner*—Thuan Dinh Dang
(74) *Attorney, Agent, or Firm*—Tenley R. Krueger

(57) ABSTRACT

Methods and processes for reducing alkylation catalyst poisoning are described herein. Such methods generally include providing a dehydrogenation system including a dehydrogenation reactor and a separation system, wherein the separation system includes a first column and a second column, introducing an alkyl aromatic hydrocarbon into the dehydrogenation reactor, contacting the alkyl aromatic hydrocarbon with a dehydrogenation catalyst disposed within the dehydrogenation reactor to form a dehydrogenation output stream comprising a vinyl aromatic hydrocarbon, passing at least a portion of the dehydrogenation output stream to first column, recovering a first overhead fraction including benzene and a first bottoms fraction from the first column, passing at least a portion of the benzene from the first column to an alkylation system including an alkylation catalyst, passing the first bottoms fraction from the first column to the second column, recovering a second overhead fraction and a second bottoms fraction from the second column, withdrawing offtest from effluent streams selected from the dehydrogenation output stream, the first bottoms fraction, the second bottoms fraction and combinations thereof to form withdrawn offtest and introducing the withdrawn offtest into the separation system downstream from the first column.

11 Claims, 2 Drawing Sheets

TREATMENT OF ALKYLATION CATALYST POISONS WITH DEHYDROGENATION

CROSS-REFERENCE TO RELATED APPLICATIONS

This application claims the benefit of U.S. patent application Ser. No. 11/361,817, filed on Feb. 24, 2006, which claims priority to U.S. Provisional Patent Application Ser. No. 60/656,464, filed Feb. 25, 2005.

FIELD

Embodiments of the present invention generally relate to minimizing alkylation catalyst poisoning.

BACKGROUND

In many processes, benzene and toluene are recovered from catalytic dehydrogenation systems and fed to alkylation/transalkylation processes. However, nitrogen compounds and other compounds present in the recovered benzene may poison the alkylation catalyst, therefore requiring more frequent regeneration and/or replacement of such catalyst.

Therefore, a need exists to utilize the recovered benzene and toluene in alkylation processes while reducing the poison effect of the nitrogen containing compound(s) and impurities on the alkylation catalyst.

SUMMARY

Embodiments of the present invention generally include a methods and processes for reducing alkylation catalyst poisoning are described herein. Such methods generally include providing a dehydrogenation system including a dehydrogenation reactor and a separation system, wherein the separation system includes a first column and a second column, introducing an alkyl aromatic hydrocarbon into the dehydrogenation reactor, contacting the alkyl aromatic hydrocarbon with a dehydrogenation catalyst disposed within the dehydrogenation reactor to form a dehydrogenation output stream comprising a vinyl aromatic hydrocarbon, passing at least a portion of the dehydrogenation output stream to first column, recovering a first overhead fraction including benzene and a first bottoms fraction from the first column, passing at least a portion of the benzene from the first column to an alkylation system including an alkylation catalyst, passing the first bottoms fraction from the first column to the second column, recovering a second overhead fraction and a second bottoms fraction from the second column, withdrawing offtest from effluent streams selected from the dehydrogenation output stream, the first bottoms fraction, the second bottoms fraction and combinations thereof to form withdrawn offtest and introducing the withdrawn offtest into the separation system downstream from the first column.

DETAILED DESCRIPTION

Introduction and Definitions

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Figure 1:
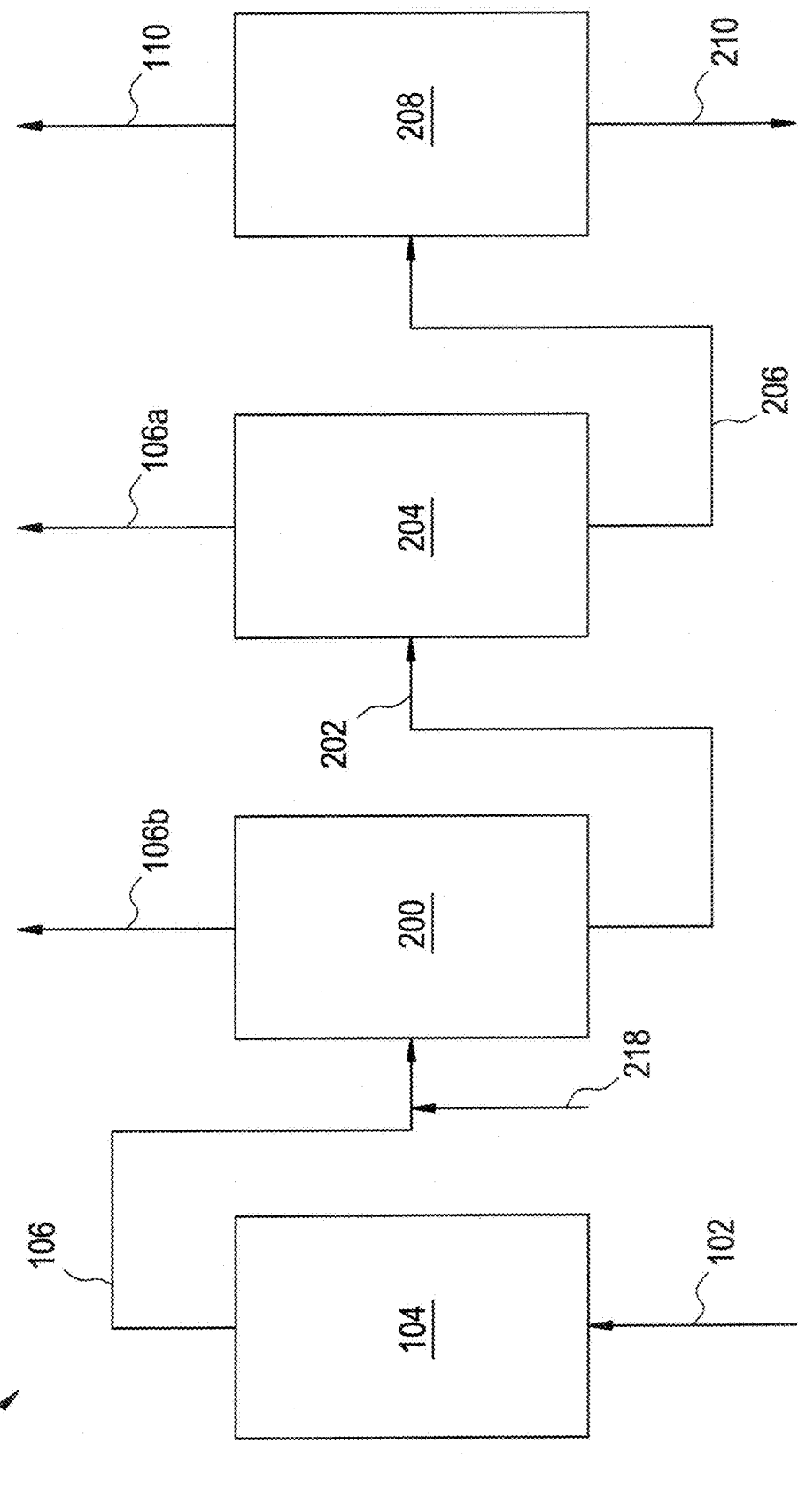
FIG. 1 illustrates a conventional dehydrogenation system.

FIG. 1 (Prior Art) illustrates an embodiment of a catalytic dehydrogenation/purification process 100. Such dehydrogenation processes generally include contacting an alkyl aromatic hydrocarbon with a dehydrogenation catalyst to form a vinyl aromatic hydrocarbon. A variety of catalysts can be used in the catalytic dehydrogenation process and are known to one skilled in the art, such as potassium iron oxide catalysts and cesium iron oxide catalysts, for example.

In FIG. 1, an input stream 102 is supplied to a dehydrogenation system 104. As used herein, individual streams will be denoted with a number, but it is generally known that such streams flow through conduits, such as pipes. The input stream 102 includes an alkyl aromatic hydrocarbon, such as ethylbenzene, for example. Steam may further be added to the input stream 102. The steam may be added to the input stream 102 in any manner known to one skilled in the art. Although the amount of steam contacting the input stream 102 is determined by individual process parameters, the input stream 102 may have a steam to alkyl aromatic hydrocarbon weight ratio of from about 0.01:1 to about 15:1, or from about 0.3:1 to about 10:1, or from about 0.6:1 to about 3:1, or from about 1:1 to about 2:1, for example.

The dehydrogenation system 104 may include any reaction vessel, combination of reaction vessels and/or number of reaction vessels (either in parallel or in series) known to one skilled in the art for the conversion of an alkyl aromatic hydrocarbon to a vinyl aromatic hydrocarbon. For example, the one or more reaction vessels may be fixed bed vessels, fluidized bed vessels and/or tubular reactor vessels.

The dehydrogenation processes discussed herein are generally high temperature processes. As used herein, the term "high temperature" refers to process operation temperatures, such as reaction vessel and/or process line temperatures (e.g., the temperature of the input stream 102 at the vessel inlet) of from about 150° C. to about 1000° C., or from about 300° C. to about 800° C., or from about 500° C. to about 700° C., or from about 550° C. to about 650° C., for example. The reaction vessel inlet will vary depending on the type of vessel.

The output 106 from the dehydrogenation system 104 (e.g., ethylbenzene and styrene) may be supplied to a first column 200 for benzene recovery. A first portion (overhead fraction) 106b (e.g., benzene and toluene) may be removed for further processing, such as alkylation/transalkylation or separation, for example. The first column 200 may include any vessel, combination of vessels and/or number of vessels (either in parallel or in series) known to one skilled in the art for the recovery of benzene from a mixed input stream. For example, the first column 200 may include one or more distillation columns.

The second portion (bottoms fraction) 202 (e.g., ethylbenzene and styrene) is sent to a second column 204 for ethylbenzene recovery. Ethylbenzene 106a is recovered from column 204 and may be recycled back to the dehydrogenation system 104 (not shown) or used for any other purpose. Line 106a may be fed to the dehydrogenation system 104 via a variety of methods, such as combination with line 102 or by directly feeding line 106a into the dehydrogenation system 104. The second column 204 may include any vessel, combination of vessels and/or number of vessels (either in parallel or in series) known to one skilled in the art for the recovery of ethylbenzene from a mixed input stream. For example, the second column 204 may include one or more distillation columns.

A bottoms fraction 206 (e.g., styrene and "heavies") may be transferred from column 204 to a third column 208 for styrene separation. Styrene 110 may be recovered and used for any suitable purpose, such as the production of polystyrene, for example. The third column 208 may include any vessel, combination of vessels and/or number of vessels (either in parallel or in series) known to one skilled in the art for the recovery of styrene from a mixed input stream. For example, the third column 208 may include one or more fractionation columns.

The bottom fraction 210 (e.g., styrene, polymer and heavies (high boiling point compounds)) may be removed and further processed, not shown. As used herein, the term "heavies" refers to higher boiling point compounds, such as indene and indane (e.g., TAR).

Offtest is generally recovered from various locations within the process 100 and may be sent to storage (not shown) prior to further processing. As used herein, the term "offtest" refers to products, such as styrene, that do not meet further processing specifications. For example, offtest may include portions of any effluent within the process 100 that do not meet product specifications. Historically, offtest is fed, either continuously or generally intermittently as needed, to column 200. However, such impurities often pass through line 106b to the alkylation process.

In addition, dehydrogenation processes may include the addition of nitrogen containing compounds (not shown) and other additives. The nitrogen containing compounds, such as amines, may be added to the dehydrogenation process for a variety of purposes, such as polymerization inhibitors and/or neutralizers, for example. In many processes, the recovered benzene and toluene, e.g., line 106b, are fed to an alkylation/transalkylation process. However, the nitrogen compounds and the other compounds present in the recovered benzene may poison the alkylation catalyst, therefore requiring more frequent regeneration and/or replacement of such catalyst. Embodiments of the present invention seek to reduce the poison effect of the nitrogen containing compound(s) and impurities on the alkylation catalyst.

Figure 2:
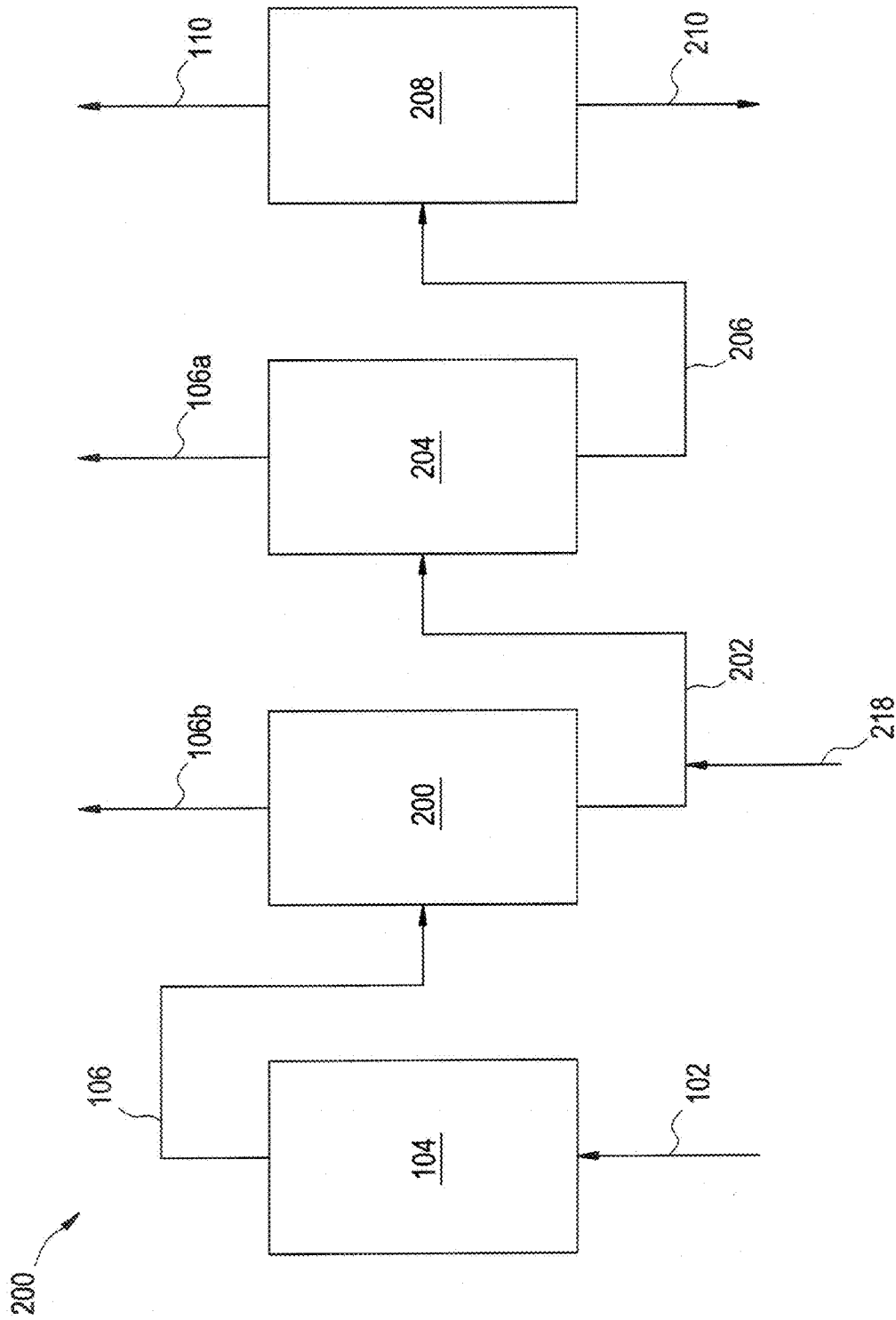
FIG. 2 illustrates an embodiment of a dehydrogenation system.

Referring to FIG. 2, the offtest 218 is fed to a location downstream of the first column, such as the second column 204, rather than back to the first column 200. The offtest 218 may be fed to column 204 via a variety of methods, such as combination with line 202 (shown) or by directly feeding line 218 into the second column 204 (not shown). Such an embodiment significantly reduces that amount of catalyst poisons passing from the first column 200 to the alkylation system. In one embodiment, the poisons pass through the second column 204 and may be recycled via line 106a back to the dehydrogenation system 104. The poisons then may burn during such reaction and not exit the system 104 via line 106. As a result, a minimal amount of impurities pass from the first column 200 to an alkylation system.

Although not shown in the Figures, additional process equipment, such as heat exchangers, may be employed throughout the process shown above and such placement is generally known to one skilled in the art.

While the foregoing is directed to embodiments of the present invention, other and further embodiments of the invention may be devised without departing from the basic scope thereof and the scope thereof is determined by the claims that follow.

What is claimed is:

1. A dehydrogenation process comprising:
   providing a dehydrogenation system comprising a dehydrogenation reactor and a separation system, wherein the separation system comprises a first column and a second column;
   introducing an alkyl aromatic hydrocarbon into the dehydrogenation reactor;
   contacting the alkyl aromatic hydrocarbon with a dehydrogenation catalyst disposed within the dehydrogenation reactor to form a dehydrogenation output stream comprising a vinyl aromatic hydrocarbon;
   passing at least a portion of the dehydrogenation output stream to the first column;
   recovering a first overhead fraction comprising benzene and a first bottoms fraction from the first column;
   passing at least a portion of the benzene from the first column to an alkylation system comprising an alkylation catalyst;
   passing the first bottoms fraction from the first column to the second column;
   recovering a second overhead fraction and a second bottoms fraction from the second column;
   withdrawing offtest from the effluent stream of the dehydrogenation reactor to form withdrawn offtest, wherein the offtest comprises effluent not meeting further processing specification
   introducing the withdrawn offtest directly into the second column separation.

2. The process of claim 1, wherein the separation system further comprises a third column.

3. The process of claim 1 further comprising introducing steam into the dehydrogenation system.

4. The process of claim 3, wherein a steam to alkyl aromatic hydrocarbon weight ratio is from about 0.01:1 to about 15:1.

5. The process of claim 1, wherein the alkyl aromatic hydrocarbon comprises ethylbenzene.

6. The process of claim 5, wherein the vinyl aromatic hydrocarbon comprises styrene.

7. The process of claim 6, wherein the output stream further comprises ethylbenzene.

8. The process of claim 1, wherein the alkylation catalyst comprises a molecular sieve catalyst.

9. The process of claim 1, wherein the dehydrogenation output stream comprises impurities.

10. The process of claim 9, wherein the impurities comprise nitrogen containing compounds.

11. The process of claim 1, wherein the alkylation catalyst deactivates at a rate that is slower than an alkylation catalyst in an identical system having offtest fed to the first column.

* * * * *